(12) United States Patent
Lamont et al.

(10) Patent No.: US 7,811,824 B2
(45) Date of Patent: Oct. 12, 2010

(54) METHOD AND APPARATUS FOR MONITORING THE PROPERTIES OF A BIOLOGICAL OR CHEMICAL SAMPLE

(75) Inventors: John Victor Lamont, Co. Antrim (IE); Robert Ivan McConnell, Co. Antrim (IE); Stephen Peter Fitzgerald, Co. Antrim (IE)

(73) Assignee: Randox Laboratories Limited, Crumlin (GB)

( * ) Notice: Subject to any disclaimer, the term of this patent is extended or adjusted under 35 U.S.C. 154(b) by 356 days.

(21) Appl. No.: 11/392,808

(22) Filed: Mar. 30, 2006

(65) Prior Publication Data

US 2007/0238181 A1    Oct. 11, 2007

(51) Int. Cl.
  *G01N 33/48* (2006.01)
  *G01N 33/483* (2006.01)
(52) U.S. Cl. ............... 436/50; 436/55; 702/19; 702/22; 702/189; 422/67
(58) Field of Classification Search ................ None
  See application file for complete search history.

(56) References Cited

U.S. PATENT DOCUMENTS

| 5,216,925 | A | 6/1993 | Odernheimer | |
|---|---|---|---|---|
| 2002/0118355 | A1* | 8/2002 | Worthington et al. | 356/72 |
| 2002/0120183 | A1* | 8/2002 | Abraham-Fuchs et al. | 600/300 |
| 2004/0199544 | A1 | 10/2004 | Balaban et al. | |
| 2005/0051723 | A1* | 3/2005 | Neagle et al. | 250/306 |

FOREIGN PATENT DOCUMENTS

| EP | 0 902 394 B1 | 3/1999 |
|---|---|---|
| WO | WO 00/50639 A2 | 8/2000 |
| WO | WO 01/16860 A2 | 3/2001 |
| WO | WO 02/064826 A2 | 8/2002 |

OTHER PUBLICATIONS

Fitzgerald, Stephen P. et al., "Development of a High-Throughput Automated Analyzer Using Biochip Array Technology," Clinical Chemistry 51:7, pp. 1165-1176, (2005).

* cited by examiner

*Primary Examiner*—P. Kathryn Wright
(74) *Attorney, Agent, or Firm*—Oliff & Berridge, PLC

(57) ABSTRACT

A method of monitoring the properties of a biological or chemical sample. The method includes carrying out a plurality of different tests on the sample to generate corresponding test data; optionally carrying out a preliminary processing of the test data to generate partially processed data; storing the test data and/or partially processed data; causing a processing system to analyze a user-defined selection of the test data or partially processed data to generate result data relating to one or more properties of the sample; and subsequent to the previous step, receiving a second user defined selection of the test data or partially processed data, different from the first selection, and causing the processing system to analyze the second user-defined selection of the test data or partially processed data to generate second result data relating to one or more properties of the sample different from the properties corresponding to the first user-defined selection.

15 Claims, 2 Drawing Sheets ents. Examples include medical diagnostics, veterinary, environmental and food quality. A particularly important example is in the clinical analysis of samples, for example for drug testing and the like.

METHOD AND APPARATUS FOR MONITORING THE PROPERTIES OF A BIOLOGICAL OR CHEMICAL SAMPLE

FIELD OF THE INVENTION

The invention relates to a method and apparatus for monitoring the properties of a biological or chemical sample.

DESCRIPTION OF THE PRIOR ART

There are a wide variety of fields in which it is desirable to monitor and determine the properties of biological or chemical samples. Examples include medical diagnostics, veterinary, environmental and food quality. A particularly important example is in the clinical analysis of samples, for example for drug testing and the like.

In many of these applications, the sample is applied to a biochip on which a number of different antibodies are immobilized and different analytes within the sample bind to the antibodies The resultant biochip array can then be analyzed to detect the presence of particular analytes leading to a determination of the individual analytes within the sample. An example of such a method using protein array technology is described in "Development of a High-Throughput Automated Analyzer Using Biochip Array Technology", Fitzgerald et al, Clinical Chemistry, 51:7, 1165-1176 (2005)

In practice, the test procedures are expensive and as a result the supply of diagnostic information is limited in many clinical situations since only a reduced number of tests can be performed per sample.

There is a need, therefore, to be able to obtain additional information on a sample in certain situations if it is found that an original selection of tests has provided insufficient information. One approach to dealing with this is described in U.S. Pat. No. 5,216,925 in which the original sample is stored so that it can be retested in the future. However, this requires very careful storage conditions to ensure that the sample retains its original properties and this is expensive and undesirable. Also no or insufficient information on interactions between analytes may be available if tests are done separately or at different times Furthermore, in many cases, sample properties can change with time in spite of storage conditions Therefore, the testing for a wide range of properties at the same time can be important In addition, if new tests have to be carried out at a later date in order to monitor status over time then additional information on earlier status can be obtained if required Knowledge of the change in status from one time to the next can be beneficial in diagnosis e.g. improvement or otherwise in patient condition. If the results of new tests suggest a change in condition then information on other properties can be obtained from most recent and earlier testing.

SUMMARY OF THE INVENTION

In accordance with a first aspect of the present invention, a method of monitoring the properties of a biological or chemical sample comprises:

a) carrying out a plurality of different tests on the sample to generate corresponding test data;

b) optionally carrying out a preliminary processing of the test data to generate partially processed data;

c) storing the test data and/or partially processed data;

d) causing a processing system to analyse a user-defined selection of the test data or partially processed data to generate result data relating to one or more properties of the sample, and e) subsequent to step (d), receiving a second user-defined selection of the test data or partially processed data, different from the first selection, and causing the processing system to analyse the second user-defined selection of the test data or partially processed data to generate second result data relating to one or more properties of the sample different from the properties corresponding to the first user-defined selection.

In accordance with a second aspect of the present invention, apparatus for monitoring the properties of a biological or chemical sample on which a plurality of different tests have been carried out to generate corresponding test data, the test data having been optionally preprocessed to generate partially processed data comprises an input device for receiving user-defined selection commands; and a processing system to analyse a user-defined selection of the test data or partially processed data to generate result data relating to one or more properties of the sample; and, in response to receiving a second user-defined selection of the test data or partially processed data, different from the first selection, to analyse the second user-defined selection of the test data or partially processed data to generate second result data relating to one or more properties of the sample different from the properties corresponding to the first user-defined selection We have realised that it is possible to separate out the different stages in analysing the properties of a sample into an initial test stage in which a number of tests are carried out on the sample itself, an optional preliminary processing stage, and a final processing stage in which results are obtained. This enables us to arrange for a large number of tests to be carried out on a sample but these test results can then be held in a store, typically a digital store, and a user can then select from the tests those for which he initially requires results. If, later, he wishes to obtain further information about the sample, Me can then choose a further selection of the test data or partially processes data. In this way, the user can control the cost of obtaining the results. He is only charged for those tests for which results are reported even though additional tests were carried out initially. This has the significant advantage that results obtained later are obtained from tests carried out simultaneously with all other tests. This ability to obtain a retrospective analysis of a sample removes the need, for example, in a clinical application to recall a patient for further sample extraction, while allowing the user such as a clinician better quality information which is conducive to a more accurate and timely diagnosis. It should also be noted that typically laboratories are only allowed to report the results of those tests that the physician/clinician orders.

A further advantage is that the efficiency of lab workflow can be improved—there is less operator intervention and no need to rerun sample which generally involves retrieval from freezer and "drawing" new sample.

In a typical application, therefore, the method will involve performing all tests that are available on a biochip while only some of those tests are selected for further analysis by a user Unprocessed test information (typically along with previously used test information) is stored allowing a user to obtain further results retrospectively.

As well as having simultaneous testing, cost and other benefits, the method can have advantages in other situations For example, in the case of drug testing, after initial results for a basic set of, often mandatory, analytes have been obtained, an "expanded" or "extended" range of test results can be easily provided subject to applicable legal or ethical requirements.

In one example, the test data comprises an image of the array of spots on a biochip. As explained above, typically each spot corresponds to a different analyte. This image data can be stored in a digital store and/or converted to a set of Relative Light Unit (RLU) values The RU values correspond to "partially processed data" and can also be stored, preferably digitally, in a memory A more detailed explanation of the generation of RLU values can be found in EP-A-0902394.

In this example, the user will submit a selection of the partially processed data, i.e identify those spots, which he wishes to analyse using the prestored RLU data, and the processing system will then carry out a conventional analysis process on the selected RLU values to generate data defining the presence or absence of the corresponding analyte(s) or to provide information on concentration with respect to a threshold corresponding to a standard concentration.

It will be recognized that other types of test data and/or partially processed data could be obtained, for example using techniques based on chemiluminescence, fluorescence, spectral absorbance, magnetic particle detection, and mass sensing. However, there are many other phenomena and techniques based thereon which can be used for assay applications such as the measurement of an analyte present in a sample. Other physical/chemical techniques include e.g. surface plasmon resonance, atomic force microscopy/chemomechanical cantilever activation.

The plurality of tests can include spectral absorbance measurements made by scanning over a range of wavelengths. Readings at specific wavelengths corresponding to concentrations of different substances in the sample would be regarded as the results of different tests.

In general, the analysis carried out by the processing system will determine one or more physical or chemical properties of the sample such as the concentration of chemical or biochemical substances in the sample.

For example, in the case of a chemiluminescence technique in conjunction with a sandwich assay, biochips are supplied with antibodies attached to the discrete test regions on a biochip When a patient sample containing the analytes of interest is added, the analytes bind to antibody sites on the surface of the biochip. Then an enzyme (i.e horseradish peroxidase) labelled antibody reagent is added which binds to a second functional group on the captured analyte. After the addition of a signal reagent (which contains a mixture of luminal/enhancer solution and peroxide), chemical reactions with the enzyme label produce light. The amount of light for this assay type is directly proportional to the analyte concentration in the patient sample. Image analysis may be carried out as described in FIG. 3, page 1171 of Clinical Chemistry 51, No 7, 2005

In order to control access to the test data and/or partially processed data, the method preferably further comprises verifying that a user can request a selection of the test data for analysis This verification can be carried out by receiving security data from a user such as a password or biometric data (fingerprint, voiceprint, eye pattern or the like) and this ensures that users can only access certain test results for which they have permission The result data can be displayed and/or stored and typically, the operation of the method will be recorded and a report logging the performance of the method generated. This enables the processing of samples to be closely monitored and also enables accurate invoicing to be achieved Thus each performance of steps (d) and (e) can be logged against the user who made the corresponding selection. In addition, details of the operator who carried out the tests in step (a) can be recorded, providing a detailed chain of custody for all samples processed.

It should be noted that, in some cases, the (same) user may carry out the testing and following initial review of results, request additional result data, i.e. carry out all steps of the method. In other situations, a laboratory technician or Test System operator may perform the initial testing of samples using an appropriate panel (group of tests) that contains those tests requested by a clinician. Results are subsequently provided to the clinician or accessed by the clinician via a network. The clinician may then directly obtain the additional result data via the network or indirectly via a request to the Test System operator or other person who may have access to the input to the processor directly or via some other local network.

Normally the results report would identify the operator/technician (for example—user of the analyzer who carried out the tests). The second results report would also identify the original test system operator and the requestor of the additional data—for accounting purposes.

It will be realized that step (e) could be repeated one or more times with further user-defined selections

BRIEF DESCRIPTION OF THE DRAWINGS

An example of a method and apparatus according to the present invention will now be described with reference to the accompanying drawings, in which.

DETAILED DESCRIPTION OF THE EMBODIMENT

Figure 1:
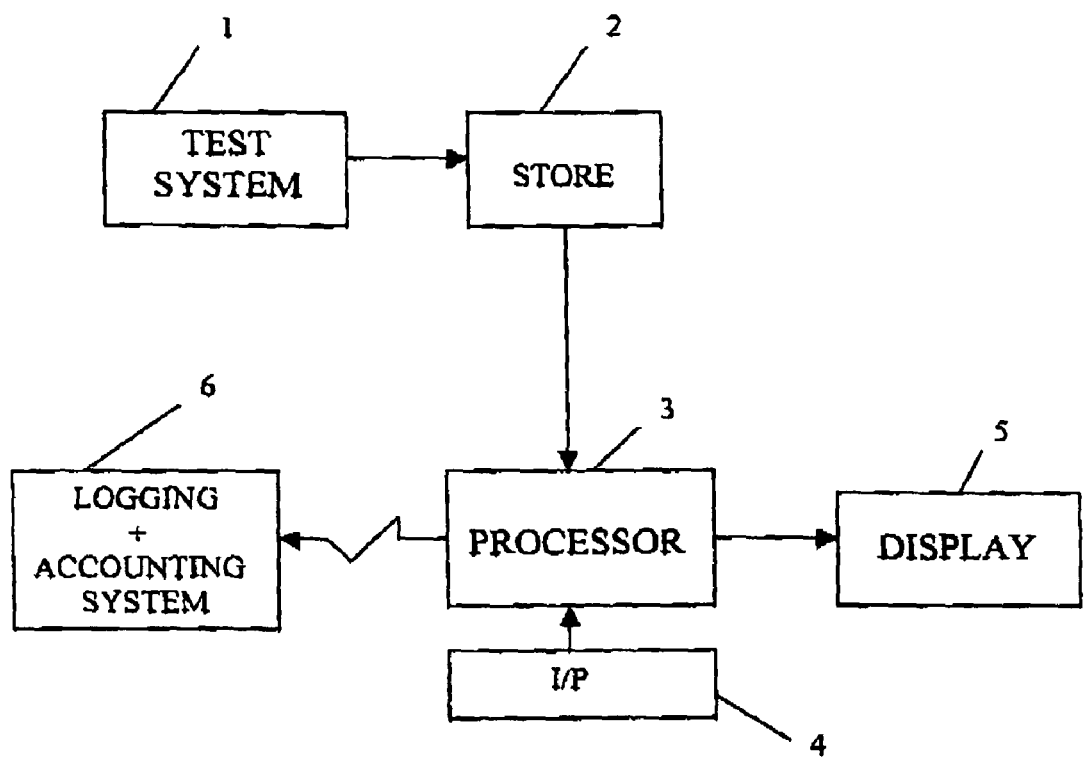
FIG. 1 is a block diagram of the apparatus.

The apparatus shown in FIG. 1 comprises a biochip test system 1 of conventional form This system is used to carry out a number of different tests on a sample by exposing the sample to an array of antigens immobilized on a biochip The system includes a digital camera which can obtain an image of the biochip array following the test process and this image is then stored in a store 2. Of course, the invention is applicable to a wide variety of complementary binding partners including any substance of biological or chemical origin such as proteins, nucleic acids, carbohydrates, lipids, drugs, chelating agents, spores, micro-organisms or cells isolated from tissue culture or blood sample or tissue biopsies. "Chemical" substances include non-biological substances such as polymers Typical examples of binding partners include, any antibody and corresponding antigen, hormone and hormone receptor, hormone and hormone binding protein, drug and drug receptor, enzyme and cofactor, transcription factor and DNA, subunits of a protein complex such as G-proteins, any signalling or transport protein and its control element, lectins and glycoproteins, lectins and carbohydrate moities, receptor protein and lipoprotein, lipid and lipoprotein, DNA and DNA, DNA and RNA, RNA and RNA, PNA and PNA, PNA and DNA, PNA and RNA, cell membrane proteins and virus, cell membrane proteins and spores, cell membrane proteins and bacteria, any cell to cell interaction through any cell surface binding protein such as MHC II and CD4.

In a typical test system, images of molecules contained in an array of discrete reaction sites on the surface of a solid support/substrate or biochip are obtained using conventional imaging apparatus, for example, a software controlled CCD camera and lens system The image is digitised by camera electronics into (for example) 512×512 pixels, of 16 bits per pixel.

A processor 3 is connected to the store 2 and receives user commands via an input device 4 such as a keyboard and/or mouse or via a wired or wireless connection, such as a LAN. The processor carries out computations on the digital data from the store 2, to be described below, to generate data defining the concentration of different analytes in the sample which is then printed and/or displayed on a monitor or other display 5. In addition, the processor 3 passes logging information to a logging and accounting system 6 which can generate invoices etc. It should be understood that the processor 3 may be connected directly to the system 6 or via an intermediate network such as a LAN, the Internet or the like. The processor could also be connected to the display 5 in this way. Also, it should be noted that the test system 1 may not necessarily be connected directly to the store 2 of the processor 3. Instead, the test system 1 could generate and store the data locally, that data then being passed to the store 2 at a later stage.

Figure 2:
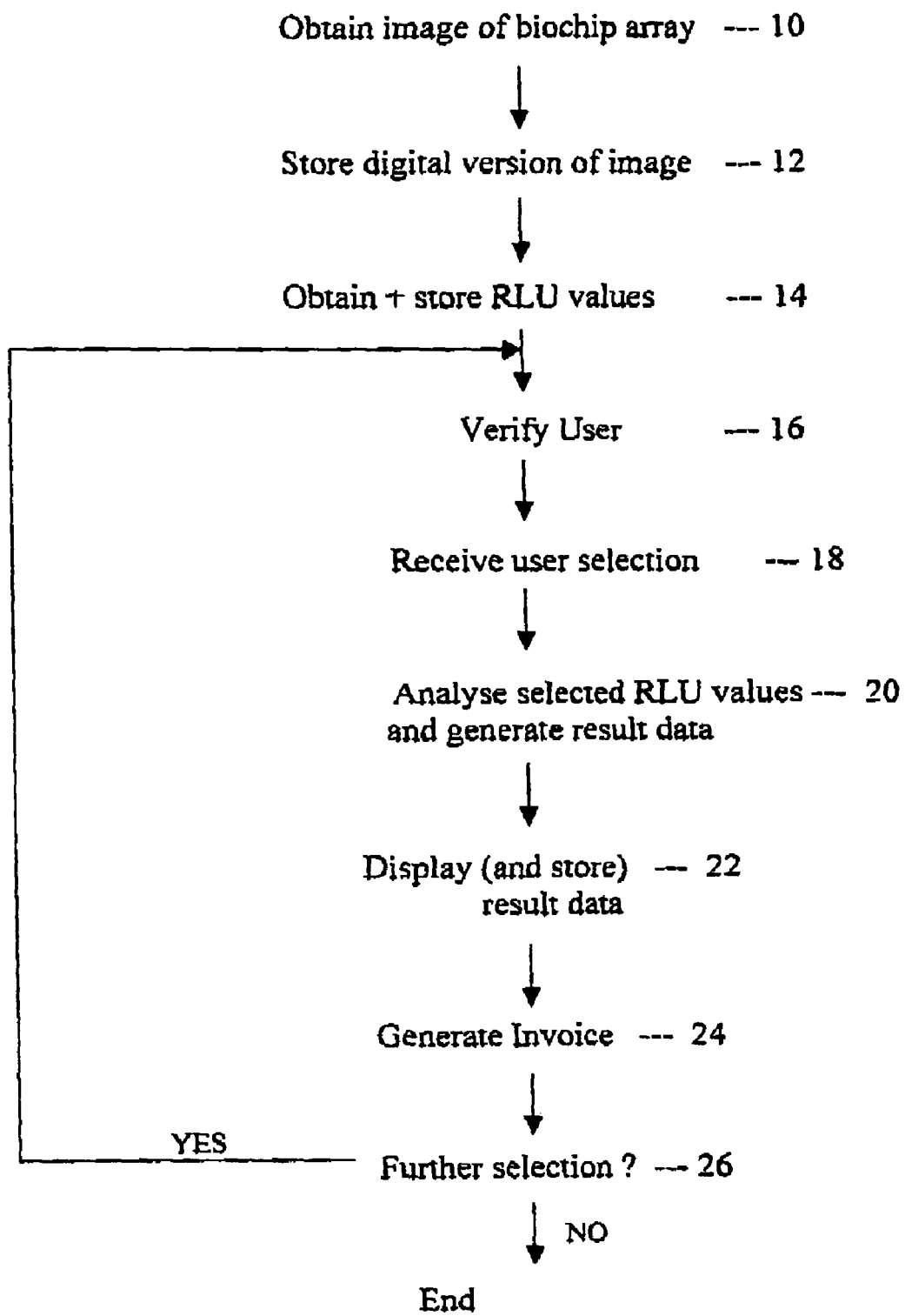
FIG. 2 is a flow diagram illustrating an example of the method.

Furthermore, the test system 1 might not generate digital data itself but rather an analogue photograph on film which is then subsequently analysed to generate the corresponding digital data FIG. 2 illustrates an example of the process. In a step 10, an image of the biochip array is obtained by the test system 1. This will typically define the image of each spot on the biochip by pixel intensity, which may also be broken down by colour component. This digital version of the image is then stored in the store 2 (step 12).

In the present example, the processor 3 then applies certain image processing algorithms to the stored data to generate light intensity values or relative light units (RLU) for each spot on the biochip. These RLU values are then stored as partially processed data in the store 2 (step 14)

In other examples, the RLU values are not computed at this stage but only in response to a user selection.

At a later point in time, a user such as a clinician will provide a user-defined selection of those analytes which he wishes to inspect via the input device 4. Initially, the processor 3 needs to verify that the user is entitled to obtain information about those analytes. Thus, a verification program is implemented (step 16) in which the user must input a user ID together with a password (or in other cases biometric data). The processor 3 then compares the input password with a prestored password in order to verify the user.

If the user is verified then the processor 3 requests the user selection which is then input by the user via the input device 4 (step 18). Typically, this can be done by presenting an array of options to the user on the display 5, those options being the analytes for which that user is authorised to obtain information. The user can then simply click on the required analytes In another option, users may only be allowed access to certain analytes.

Once the user selection has been completed, the processor 3 accesses the relevant RLU values from the store 2 and using stored calibration data converts the RLU values into concentration data for each analyte (step 20) Depending on the user requirements, this concentration data may be presented as quantitative values and/or categorised into positive or negative relative to a cut-off concentration selected by the user. This information is displayed on the display 5 (step 22) and may also be stored.

Concentrations of chemicals or biochemical substances in the sample under test may be recorded along with the sample ID. Each concentration may be accompanied with additional information/indicators highlighting whether the value is above, below (or borderline) with respect to some particular value which the operator has predefined. Associated information may include: Date, User name, Machine No., batch numbers and expiry date for reagents, calibration information (Pass, date, time, expiry date) for calibration and for calibrants.

In a wider context, the approach could be applied to parameters other than concentration, for example, any physical or chemical property of the sample or its constituents.

Information relating to the user selection is also sent by the processor 3 to the logging and accounting system 6 where the selection is logged against the identification of the user In addition, the system 6 can generate an invoice reflecting the fee for obtaining the particular selected analyte information (step 24). Step 24 may be omitted at this stage if a different business model is agreed with test laboratories and the like for the supply of instrumentation and testing products. Also, after step 22, details of the use of the results may be logged for subsequent generation of an invoice relating to the extent of results reported.

The same or another authorized user can at a later date carry out a retrospective analysis of the original data as stored in the store 2. If a further analysis is to be performed (step 26) processing returns to step 16. Ultimately, a further invoice is then generated in a step 24.

In the example described, the raw test data is in the form of an image of the biochip array Other forms of raw test data can be obtained depending on the measurement techniques, methodologies and technologies employed. These can include chemiluminescence, fluorescence, spectral absorbance, magnetic particle detection, and mass sensing. In some cases, the raw data output can be recorded as an image file from an imaging sensor, whilst in others the output from one or more discrete sensors or sensor systems may be stored digitally in other appropriate file formats Calibration data and derived calibration curves will also be stored for future recall and additional result provision Indeed, a particular advantage of the present invention is that if a new algorithm is devised for analysing the original test data, this can be applied by the processor 3 at a later date.

A particular example in which retrospective analysis would be used will now be described.

A simple example is in thyroid function testing

TSH (Thyroid Stimulating Hormone) is a major regulator of the thyroid gland and stimulates the release of T3 and T4 (Tri-iodothyronine and Thyroxine respectively)

Often a clinician will request checks an the levels of TSH and possibly also Free T4 (i.e unsound T4). Based on the levels of TSH (and T4) he may then request measurements of other(s) i.e. Free T3.

A second example is allergy testing for specific IgEs (Immunoglobulin E), in patient samples. The term allergen is used to describe the protein that the body does not recognize as safe and in response the body produces IgE antibodies to the substance which in turn trigger mast cells to release chemicals such as histamines that cause inflammation within the body In the case of allergies to grass pollen, a mixture of grass pollen from different species can define a discrete test region on a biochip array. Pollen allergens from individual grass species may be applied separately to define other test regions on the same biochip.

Should the result of the test using the mixture indicate an allergic response then the results for the selected individual grasses can be obtained from specific IgE measurements obtained via retrospective analysis.

Immunoglobulin Ig

A general term for the kind of globular blood proteins that constitute antibodies A tetrameric protein composed of two identical light chains and two identical heavy chains. Specific proteins produced by derivatives of B lymphocytes that interact with and help protect an organism from specific antigens.

Immunoglobulin E (IgE)

One of five classes of immunoglobulins made by humans (the others being IgA, IgD, IgG and IgM).

Note The requirement for additional information may arise in the following situations.

1) The need by clinicians, following examination of the initial/basic/results, for further information to assist them in a fuller and potentially more rapid diagnosis and then treatment
2) A similar requirement in veterinary, food, environmental or other sectors.
3) Selective reporting for the drugs of abuse is an important feature due to legal and ethical issues. Validity of drug tests results requires a number of different issues to be considered including sample stability, cross reactivity and sample adulteration. The simultaneous measurement capability afforded by biochip array technology (Such as Evidence Biochip Array Technology and Analyzer from Randox Laboratories Ltd) ensures that regardless of when the request is made, the results from the sample will have been taken at exactly the same point in time
    In certain situations, time restrictions may be imposed by medical need, legal or other factors and can limit the number of tests or additional/subsequent tests which can conventionally be carried out in the time available.
4) Other situations when this may be useful will include use for clinical trials or patient studies when the clinician only has ethical approval for a selection of biomarkers. As the study progresses, it may appear useful to look at another marker and this information can be retrieved at a later date if required, and after appropriate ethical approvals have been received.
5) In the environmental sector, many compounds of interest are structurally very similar. It can be of benefit to be able to look back to results for related compounds

We claim:

1. A method of monitoring the properties of a biological or chemical sample, the method comprising:
    a) carrying out a plurality of different tests on the sample to generate corresponding test data;
    b) optionally carrying out a preliminary processing of the test data to generate partially processed data;
    c) storing the test data and/or partially processed data in a test system;
    d) verifying that a user is authorized to request a specific first user-defined selection of the stored test data or partially processed data for analysis and, if said user is authorized, causing a processing system to analyze the first user-defined selection of the test data or partially processed data to generate a first set of result data relating to one or more properties of the sample, and reporting said first set of result data to said user;
    e) recording in the test system which data or partially processed data was analyzed to generate said first set of result data, generating a first fee invoice specific to said first set of result data, and marking the first set of result data in the test system as having been reported to said user;
    f) subsequent to step (d), verifying that said user is authorized to request a specific second user-defined selection of the stored test data or partially processed data and, if said user is authorized, causing the processing system to analyze the second user-defined selection of the test data or partially processed data to generate a second set of result data relating to one or more properties of the sample different from the properties corresponding to the first user-defined selection, and reporting said second set of result data to said user; and
    g) recording in the test system which data or partially processed data was analyzed to generate said second set of result data, generating a second fee invoice specific to said second set of result data, and marking the second set of result data in the test system as having been reported to said user.

2. A method according to claim 1, wherein the verification process includes the verification of security data supplied by the user.

3. A method according to claim 2, wherein the security data comprises password or biometric data.

4. A method according to claim 1, wherein the result data is displayed and/or stored.

5. A method according to claim 4, wherein the display is carried out on a monitor and/or printer.

6. A method according to claim 1, further comprising generating a report logging the performance of the method.

7. A method according to claim 6, wherein the report identifies each performance of steps (d) and (f) against the user who defined the corresponding selection.

8. A method according to claim 1, wherein the test data includes images of radiation emitted from an array of discrete reaction sites after testing for respective analyses.

9. A method according to claim 1, wherein the partially processed data comprises relative light unit values from an array of discrete reaction sites after testing for respective analyses.

10. A method according to claim 1, wherein the tests are selected from chemiluminescence, fluorescence, spectral absorbance, magnetic particle detection, and mass sensing.

11. A method according to claim 1, wherein the analyses carried out in steps (d) and (f) determine the concentrations of chemical or biochemical substances in the sample.

12. A method according to claim 1, wherein the analyses carried out in steps (d) and (f) determine one or more physical or chemical properties of the sample.

13. A method according to claim 1, wherein the test data or partially processed data is stored in a digital store of a processing system.

14. A method according to claim 1, wherein the verifying steps in steps (d) and (f) are specific to one or more predetermined analytes.

15. A method according to claim 14, wherein the tests in step (a) are carried out at the same time.

* * * * *